United States Patent
King et al.

(10) Patent No.: US 6,999,898 B2
(45) Date of Patent: Feb. 14, 2006

(54) CLASSIFICATION OF DEVIATIONS IN A PROCESS

(75) Inventors: Karl L. King, Windsor, CO (US); Ziyi Wang, Louisville, CO (US); Dan J. Kroll, Fort Collins, CO (US)

(73) Assignee: Hach Company, Loveland, CO (US)

( * ) Notice: Subject to any disclaimer, the term of this patent is extended or adjusted under 35 U.S.C. 154(b) by 74 days.

(21) Appl. No.: 10/751,168

(22) Filed: Dec. 31, 2003

(65) Prior Publication Data

US 2004/0158432 A1 Aug. 12, 2004

Related U.S. Application Data

(60) Provisional application No. 60/438,358, filed on Jan. 7, 2003.

(51) Int. Cl.
G06F 3/023 (2006.01)

(52) U.S. Cl. .................. 702/183; 702/182; 702/187; 702/188

(58) Field of Classification Search ............ 702/27, 702/38, 58, 60, 182, 183, 187, 188; 324/693; 700/28, 108; 704/209; 205/742, 743
See application file for complete search history.

(56) References Cited

U.S. PATENT DOCUMENTS

| | | | |
|---|---|---|---|
| 4,017,734 A | 4/1977 | Ross | 250/431 |
| 5,368,826 A | 11/1994 | Weltz et al. | 422/243 |
| 5,469,369 A * | 11/1995 | Rose-Pehrsson et al. | 702/27 |
| 5,583,951 A | 12/1996 | Sirat et al. | 382/232 |
| 5,680,409 A | 10/1997 | Qin et al. | 371/48 |
| 5,748,508 A | 5/1998 | Baleanu | 364/578 |
| 6,301,572 B1 * | 10/2001 | Harrison | 706/52 |
| 6,332,110 B1 | 12/2001 | Wolfe | 702/22 |
| 6,405,140 B1 | 6/2002 | Chen et al. | 702/35 |
| 6,408,259 B1 | 6/2002 | Goebel et al. | 702/183 |
| 6,408,321 B1 | 6/2002 | Platt | 708/520 |
| 6,442,639 B1 | 8/2002 | McElhattan et al. | 710/303 |
| 6,560,543 B1 | 5/2003 | Wolfe et al. | 702/22 |
| 6,669,838 B1 | 12/2003 | Baarman | 210/85 |
| 6,780,306 B1 * | 8/2004 | Schlager et al. | 205/701 |
| 2003/0109951 A1 * | 6/2003 | Hsiung et al. | 700/108 |
| 2004/0006513 A1 | 1/2004 | Wolfe | 705/22 |
| 2004/0020862 A1 | 2/2004 | Baca et al. | |
| 2004/0138840 A1 | 7/2004 | Wolfe | 702/81 |

OTHER PUBLICATIONS

Jolliffe, I. T., "Principal Component Analysis," Second Edition, Springer Verlag, New York, 1986.

* cited by examiner

Primary Examiner—Marc S. Hoff
Assistant Examiner—Felix Suarez
(74) Attorney, Agent, or Firm—Setter Ollila LLC

(57) ABSTRACT

A process analysis system includes sensors and a processing system. The sensors monitor the process to generate sensor signals. The processing system processes the sensor signals to detect a deviation from a baseline for the process. The processing system generates a process vector for the deviation in response to detecting the deviation. The processing system compares the process vector to a plurality of library vectors to classify the deviation. In some examples, the process comprises a system that supplies water.

32 Claims, 5 Drawing Sheets

CLASSIFICATION OF DEVIATIONS IN A PROCESS

RELATED CASES

This patent claims the benefit of U.S. provisional patent application Ser. No. 60/438,358, entitled "Classification of Deviations in a Process", filed on Jan. 7, 2003, and which is hereby incorporated by reference into this patent.

BACKGROUND OF THE INVENTION

1. Field of the Invention

The invention is related to the field of process analysis, and in particular, to technology that classifies deviations in the process.

2. Statement of the Problem

Sensors measure the characteristics of a process. Such processes include water supply systems, manufacturing operations, electrical distribution systems, and communication systems. For example, water supply systems use sensors to measure pressure, temperature, and flow rate. Unfortunately, sensors have not been developed to detect every abnormal condition. There may not be available sensors to detect if a specific component fails, or to detect a specific contaminant in the process. Typically, it is too complex and expensive to develop a new sensor for each new abnormal condition of interest.

SUMMARY OF THE SOLUTION

Some examples of the invention include process analysis systems and their methods of operation. The process analysis systems include a plurality of sensors and a processing system. The sensors are configured to monitor the process to generate sensor signals. The processing system is configured to process the sensor signals to detect a deviation from a baseline for the process, generate a process vector for the deviation in response to detecting the deviation, and compare the process vector to a plurality of library vectors to classify the deviation.

In some examples of the invention, the process comprises a system that supplies water.

In some examples of the invention, the sensor signals indicate pH, conductivity, turbidity, chlorine, and total organic carbon of the water.

In some examples of the invention, the classified deviation comprises a contaminant in the water.

In some examples of the invention, the processing system is configured to signal a control system to operate a valve in response to classifying the deviation as a contaminant in the water.

In some examples of the invention, the processing system is configured to signal a control system to add a marker to the water in response to classifying the deviation as a contaminant in the water.

In some examples of the invention, the marker comprises a colorant.

In some examples of the invention, the processing system is configured to signal a control system to perform a treatment on the water in response to classifying the deviation as a contaminant in the water.

In some examples of the invention, the treatment comprises adding a disinfectant to the water.

In some examples of the invention, the treatment comprises adding chlorine to the water.

In some examples of the invention, the treatment comprises exposing the water to ultraviolet radiation.

In some examples of the invention, the processing system is configured to process the sensor signals to produce a single variable and compare the single variable to a threshold to detect the deviation from the baseline.

In some examples of the invention, the process vector comprises a unit vector.

In some examples of the invention, the processing system is configured to compare an angle between the process vector and one of the library vectors to a threshold.

In some examples of the invention, the library vectors are associated with abnormal operations and the processing system is configured to identify one of the abnormal operations that is associated with one of the library vectors that matches the process vector to classify the deviation.

In some examples of the invention, the processing system is configured to store the process vector as a new one of the library vectors and associate an abnormal operation with the new library vector in response to an unknown classification.

DESCRIPTION OF THE DRAWINGS

The same reference number represents the same element on all drawings.

DETAILED DESCRIPTION OF THE INVENTION

FIGS. 1–5 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

EXAMPLE #1

Figure 1:
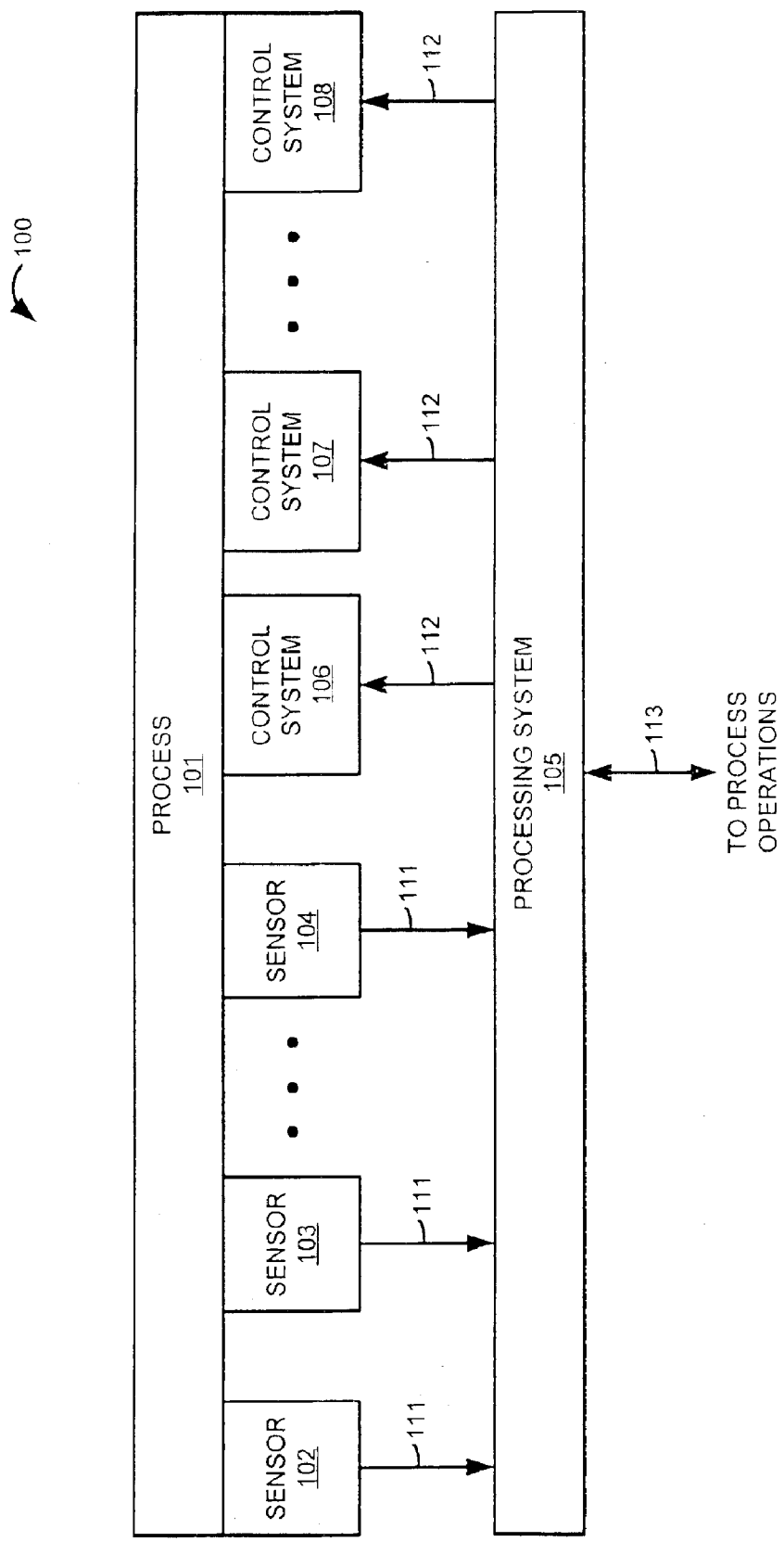
FIG. 1 illustrates a process analysis system in an example of the invention.

FIG. 1 illustrates process analysis system 100 in an example of the invention. Process analysis system 100 includes process 101, sensors 102–104, processing system 105, and control systems 106–108. The number of sensors and control systems shown on FIG. 1 has been restricted for clarity.

Process 101 is a dynamic operation that is characterized by multiple parameters that can be measured by sensors 102–104. Process 101 could be a water supply system, manufacturing operation, electrical distribution system, communication system, or some other process that is suitable for the analysis of system 100.

Sensors 102–104 measure characteristics of process 101 and transfer sensor signals 111 to processing system 105.

Sensor signals 111 indicate the measured characteristics, and thus, provide information about the current state of process 101. For a water supply system, sensors 102–104 may measure pH, conductivity, turbidity, chlorine, total organic carbon and other characteristics of the water flowing through a water main.

Control systems 106–108 exert control over process 101 in response to control signals 112 from processing system 105. For a water supply system, control systems 106–108 may operate valves on the water main, add a selected marker to the water in the water main, or perform some other treatment. The marker could include a colorant to mark contaminated water. The treatment could counteract contaminants through the addition of a disinfectant to the water, the exposure of the water to ultraviolet radiation, or some other treatment.

Processing system 105 processes sensor signals 111 to identify a deviation from a baseline for process 101. In response to identifying the deviation, processing system 105 generates a process vector for the deviation and compares the process vector to a plurality of library vectors to classify the deviation. Processing system 105 may provide control signals 112 to control systems 106–108 based on the classified deviation. Processing system 105 may also provide analysis data 113 to process operations.

For the water supply system, processing system 105 may identify and classify a deviation indicating water contamination, and in response, instruct control systems 106–108 to operate valves that will shut off or divert the supply of contaminated water. In addition, processing system 105 may provide a contamination alarm to water supply operations.

Processing system 105 could include a computer, microprocessor, digital signal processor, application specific integrated circuitry, special purpose circuitry, or some other processing apparatus. Processing system 105 may execute instructions that direct processing system 105 to operate as described herein. The instructions could include software, firmware, programmed integrated circuitry, or some other form of machine-readable instructions. Thus, a product may be comprised of a memory that stores the instructions. The memory could be comprised of a disk, tape, integrated circuit server, or some other memory device. Processing system 105 could be a single device or a set of interoperating devices. Processing system 105 could be located at a single site or distributed over a wide geographic area.

EXAMPLE #2

Figure 2:
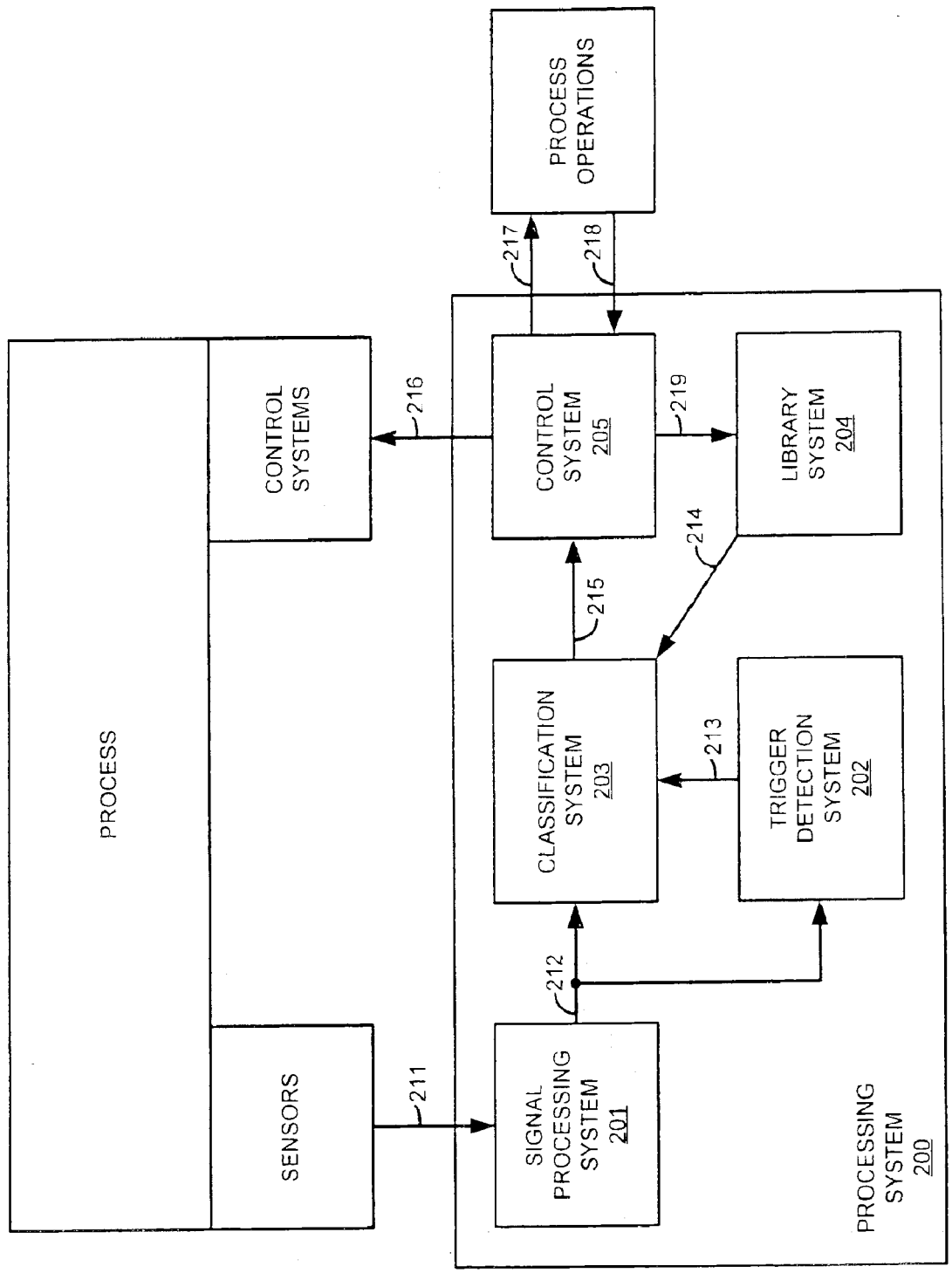
FIG. 2 illustrates a processing system in an example of the invention.

FIG. 2 illustrates processing system 200 in an example of the invention. Processing system 200 is an example of processing system 100 of FIG. 1. Processing system 200 includes signal processing system 201, trigger detection system 202, classification system 203, library system 204, and control system 205.

Signal processing system 201 receives sensor signals 211 from the sensors that measure process characteristics. Signal processing system 201 processes sensor signals 211 to provide processed sensor data 212 to trigger detection system 202 and classification system 203. The signal processing could entail reformatting the sensor signals, removing noise, replacing missing or false data, or other operations that prepare sensor data 212 for systems 202–203. Replacement data could be the last known good value, an average value, or a user-selected default value. If data is replaced a given number of times within a specific time period, then an appropriate alarm could be generated.

Trigger detection system 202 receives processed sensor data 212. Trigger detection system 202 processes sensor data 212 to determine if there is a deviation from a baseline for the process. In response to detecting a deviation from the baseline, trigger detection system 202 provides trigger indication 213 to classification system 203. To detect the deviation from baseline, trigger detection system 202 may process sensor data 212 to produce a single logical variable whose state indicates whether the process is operating normally or abnormally. When the process is operating abnormally, the single logical variable should cause a trigger. One example of a single logical variable is the angle between two unit vectors, where one unit vector is derived from sensor data 212 and the other unit vector from a vector library and is associated with an abnormal operation. Trigger detection techniques include sensor data thresholds, genetic algorithms, pattern recognition, neural networks, process modeling, statistical methods, or another suitable approach to trigger detection.

Classification system 203 receives processed sensor data 212 and trigger indication 213. In response to trigger indication 213, classification system 203 processes sensor data 212 to classify the deviation. To classify the deviation, classification system 203 processes sensor data 212 to generate a process vector. The process vector represents the current state of the process—where the process may be operating abnormally as indicated by the trigger.

Classification system 203 also retrieves vector library 214 from library system 204. Vector library 214 includes a set of stored library vectors and their associated abnormal operations. Examples of abnormal operations include component failure, contamination, operator error, unauthorized intrusion, or some other unwanted event that negatively affects the process. The stored library vectors are previously derived through the observation of actual abnormal operations or through tests that emulate various abnormal operations in order to associate a specific abnormal operation with a specific library vector. These observations and tests should use the same type of sensors and processing that produce the process vector.

Classification system 203 compares the process vector to the library vectors to find a match. The match does not have to be absolute, and typically, two vectors are deemed a match if they are within a specified range or angle of one another. Various techniques can be used to determine a match between two vectors, including a minimum angle analysis, a minimum distance calculation, nearest neighbor analysis, or some other vector comparison technique. If the process vector matches one of the library vectors, then the deviation is classified based on the abnormal operation that is associated with the matching library vector. If the process vector does not match any of the library vectors, then the deviation is classified as unknown. In response to classification of the deviation, classification system 203 transfers deviation classification 215 to control system 205.

Control system 205 receives and processes deviation classification 215 to provide control instructions 216 to the process control systems and to provide alarms 217 to process operations. The selection of control instructions and alarms could be based on a look-up table that associates specific control instructions and alarms with specific abnormal operations. Control instructions 216 and alarms 217 are used to initiate remedial action that counters the abnormal operation.

For unknown classifications, deviation classification 215 and alarms 217 indicate the process vector with the unknown classification and its associated sensor data 212. Classification system 203 typically associates a unique reference number with each process vector and its classification, and process vectors with unknown classifications may be distinguished by their reference number. Personnel at process operations investigate the deviation to determine the associated abnormal operation. Process operations provide vector information 218 to control system 205. Vector information 218 specifies a new library vector—which was the process unit vector that previously had an unknown classification. Vector information 218 also specifies the abnormal operation to associate with the new library vector as determined by process operations. Vector information 218 also indicates the control signals and alarms that should be implemented upon subsequent classification of the abnormal operation based on the new library vector. Control system 205 provides library update 219 to library system 204. Library update 219 specifies the new library vector and its associated abnormal operation. Library system 204 stores the new library vector and its associated abnormal operation in unit vector library 214. Thus, future occurrences of the abnormal operation will be automatically classified, so the proper remedial action can be promptly implemented. Vector library 214 could be distributed and shared among different processing systems at various locations, so that an abnormal operation discovered at one location may subsequently be automatically classified and countered at a different location.

If desired, the vector library may be separated into vector groups. For example, one vector group could be contamination and a second vector group could be equipment malfunction. The sequence of the vector comparisons could be established based on the groups, so that high impact vector groups are processed before lower impact vector groups. Thus, the library vectors for dangerous contaminants could be checked before the library vectors for minor equipment malfunctions are checked.

EXAMPLE #3

Figure 3:
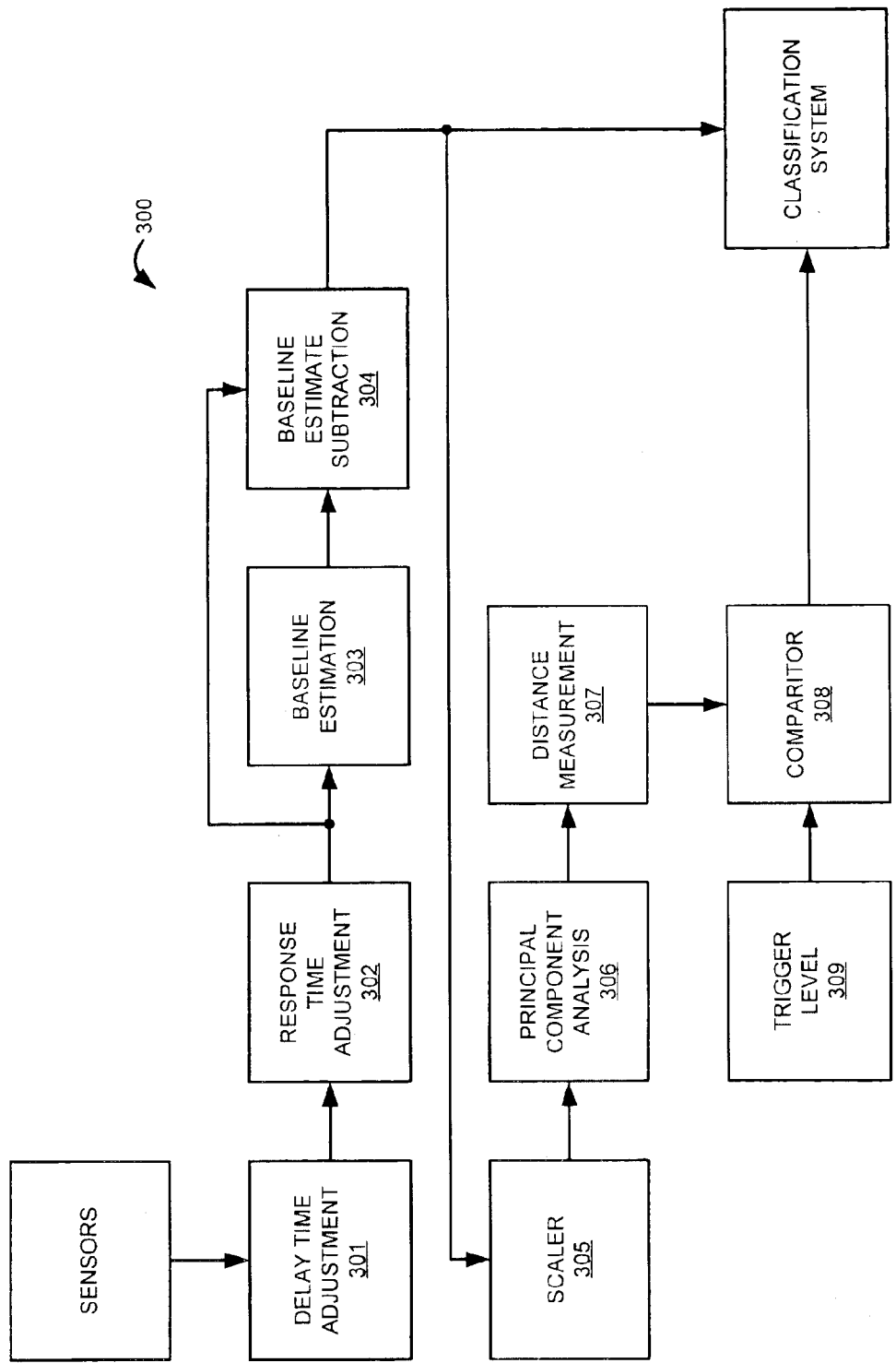
FIG. 3 illustrates a signal processing and trigger detection system in an example of the invention.

FIG. 3 illustrates signal processing and trigger detection system 300 in an example of the invention. Signal processing and trigger detection system 300 is an example of signal processing system 201 and trigger detection system 202 of FIG. 2. Signal processing and trigger detection system 300 includes delay time adjustment 301, response time adjustment 302, baseline estimation 303, baseline estimate subtraction 304, scaler 305, principal component analysis 306, distance measurement 307, comparator 308, and trigger level 309. Delay time adjustment 301 receives various sensor signals from a number of sensors for the process. Delay time adjustment 301 time shifts the sensor signals to align the signals in time. This typically involves delaying the signals that arrive early to match the slowest signal in the time domain. Delay time adjustment 301 transfers time shifted signals to response time adjustment 302.

Response time adjustment 302 shifts the slopes of the time shifted signals to align their response times. For example, response time adjustment 302 could use a linear filter to alter the response times of faster signals to match the response time of the slowest signal. Response time adjustment 302 transfers time and response adjusted signals to baseline estimation 303 and to baseline estimate subtraction 304.

Baseline estimation 303 processes the time and response adjusted signals to determine baseline values for the sensor signals. Baseline estimation could utilize a moving window average, a Kalman filter that takes into account both process noise statistics and measurement noise statistics, or some other baseline determination technique. Baseline estimation 303 transfers baseline estimates to baseline estimate subtraction 304.

Baseline estimate subtraction 304 receives both the time and response adjusted signals and the baseline estimates. Baseline estimate subtraction 304 subtracts the baseline estimates from their respective time and response adjusted signals to determine a difference from the baseline estimate for each of the sensor signals. Baseline estimate subtraction 304 transfers these differences from the baseline estimates to scaler 305 and to the classification system.

Scaler 305 adjusts the differences based on weighting factors that are specific to the type of difference. Typically, scaler 305 multiplies each difference by a specific weighting factor to normalize the differences, so that one difference does not vary disproportionately to the other differences. Scaler 305 transfers the scaled differences to principal component analysis 306.

Principal component analysis 306 processes the scaled differences using principal component analysis techniques to reduce the data set. For example, if there are five sensor signals, then there are five scaled differences. Some of the scaled differences may share redundant information. Principal component analysis 306 combines sets of scaled differences that share redundant information to reduce the data set. In an example with five sensor signals, it may be possible to combine a two of the scaled differences into one difference to reduce the data set from five to four differences. Other techniques to reduce the data set and remove redundancy could be used, or principal component analysis 306 could be omitted altogether. Principal component analysis 306 transfers the resulting scaled differences to distance measurement 307.

Distance measurement 307 processes the resulting scaled differences to derive one logical variable that can be used to initiate the classification process if the one logical variable exceeds a threshold. The logical variable could be derived by squaring each of the resulting scaled differences and then summing the squares. Distance measurement 307 transfers the logical variable to comparator 308.

Trigger level 309 provides a trigger level to comparator 308. The trigger level could be set by process operations, determined through empirical testing, determined based on historical process data, or derived through another suitable technique. To determine the trigger level based on historical process data, a Ljung-Box lack-of-fit analysis could be performed to determine a trigger level that indicates when current differences deviate from historical differences.

Comparator 308 receives the logical variable and the trigger level. Comparator 308 compares the logical variable to the trigger level to determine if the logical variable exceeds the threshold specified by the trigger level. If the logical variable exceeds the trigger level, then a deviation is detected, and comparator 308 generates a trigger signal and transfers the trigger signal to the classification system to initiate classification of the deviation.

Figure 4:
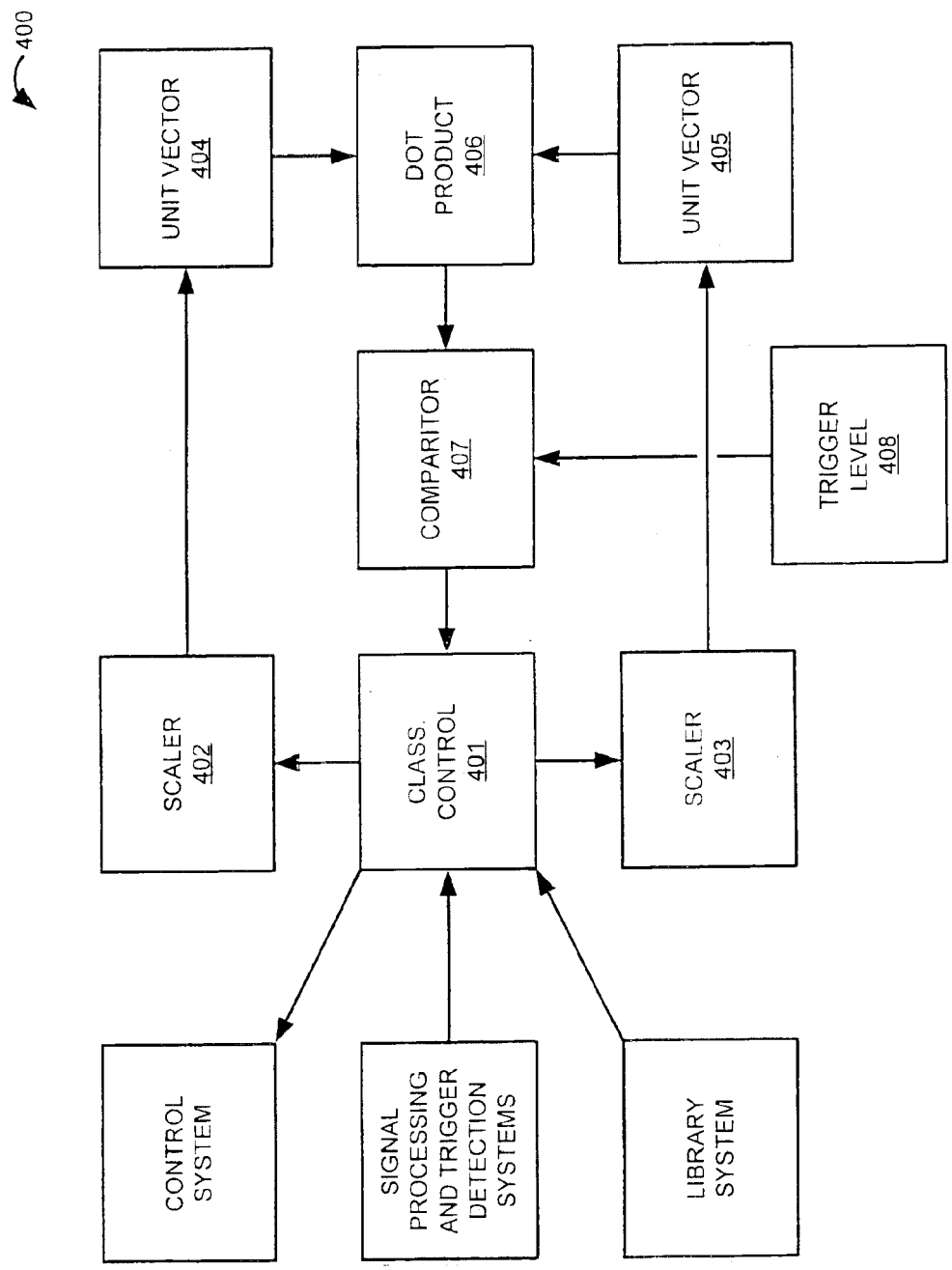
FIG. 4 illustrates a classification system in an example of the invention.

FIG. 4 illustrates classification system 400 in an example of the invention. Classification system 400 is an example of classification system 203 FIG. 2. Classification system 400 includes classification control 401, scalers 402-403, unit vectors 404-405, dot product 406, comparator 407, and trigger level 408.

Classification control 401 receives the differences from the baseline estimates and the trigger signal from the signal processing and trigger detection systems. In response to the trigger signal, classification control 401 logs the date, time, reference number, and differences for the trigger. In addition, classification control 401 retrieves a vector library from the library system. Classification control 401 transfers the differences to scaler 402 and transfers library vectors from the vector library to scaler 403.

Scaler 402 adjusts the differences based on a weighting factor specific to each type of difference. Scaler 402 transfers the scaled differences to unit vector 404. Scaler 403 adjusts the library vectors based on weighting factors that are specific to each component of the library vectors. Scaler 403 transfers the scaled library vectors to unit vector 405. Typically, scalers 402 and 403 apply the same weighting factors to the same vector components.

Unit vector 404 processes the scaled differences to generate a process unit vector. The process unit vector has a magnitude of one and an angle. Unit vector 404 transfers the process unit vector to dot product 406.

Unit vector 405 processes the scaled library vectors to generate library unit vectors. The library unit vectors also have a magnitude of one and their respective angles. Unit vector 404 transfers the library unit vectors to dot product 406.

One technique of obtaining a process unit vector is to divide each difference by the square root of the sum of the squares of all differences to produce a vector whose geometrical length is unity. The information about the magnitude of the process vector is lost by design, but the information about the angle of the process vector is retained. Advantageously, the use of a unit vector tends to work well regardless of the magnitude of the deviation.

Dot product 406 receives the process unit vector and the library unit vectors. To get the angle between the process unit vector and an individual library unit vector, dot product 406 calculates the arc-cosine of the dot product of the process unit vector and the individual library unit vector. Dot product 406 repeats the calculation for all of the library unit vectors and transfers the resulting angles to comparator 407.

If desired, the unit vector and dot product steps described above could be combined into a single processing step to produce the angles from the scaled differences and scaled library vectors. Alternatively, the use of unit vectors could be omitted, and the process vector and the library vectors could be compared through some other technique to determine a match.

Trigger level 408 stores a trigger level that indicates how close an angle must be between the process unit vector and a given library unit vector to find a match. The trigger level can be set through empirical testing or by process operations. Trigger level 408 provides the trigger level to comparator 407.

Comparator 407 receives the angles and the trigger level. Comparator 407 compares the angles to the trigger level to determine if any of the angles fall below the trigger level. If one of the angles falls below the trigger level, then comparator 407 generates a match signal and transfers the match signal to classification control 401.

In response to the match signal, classification control 401 classifies the deviation by determining the specific abnormal operation that is associated with the library vector that produced the match. Classification control 401 transfers the classified deviation to the control system. If all of the library vectors are compared without a match, then classification control 401 transfers an unknown classification to the control system, along with the reference number, deviations, and other desired data that is associated with the unknown classification.

EXAMPLE #5

Figure 5:
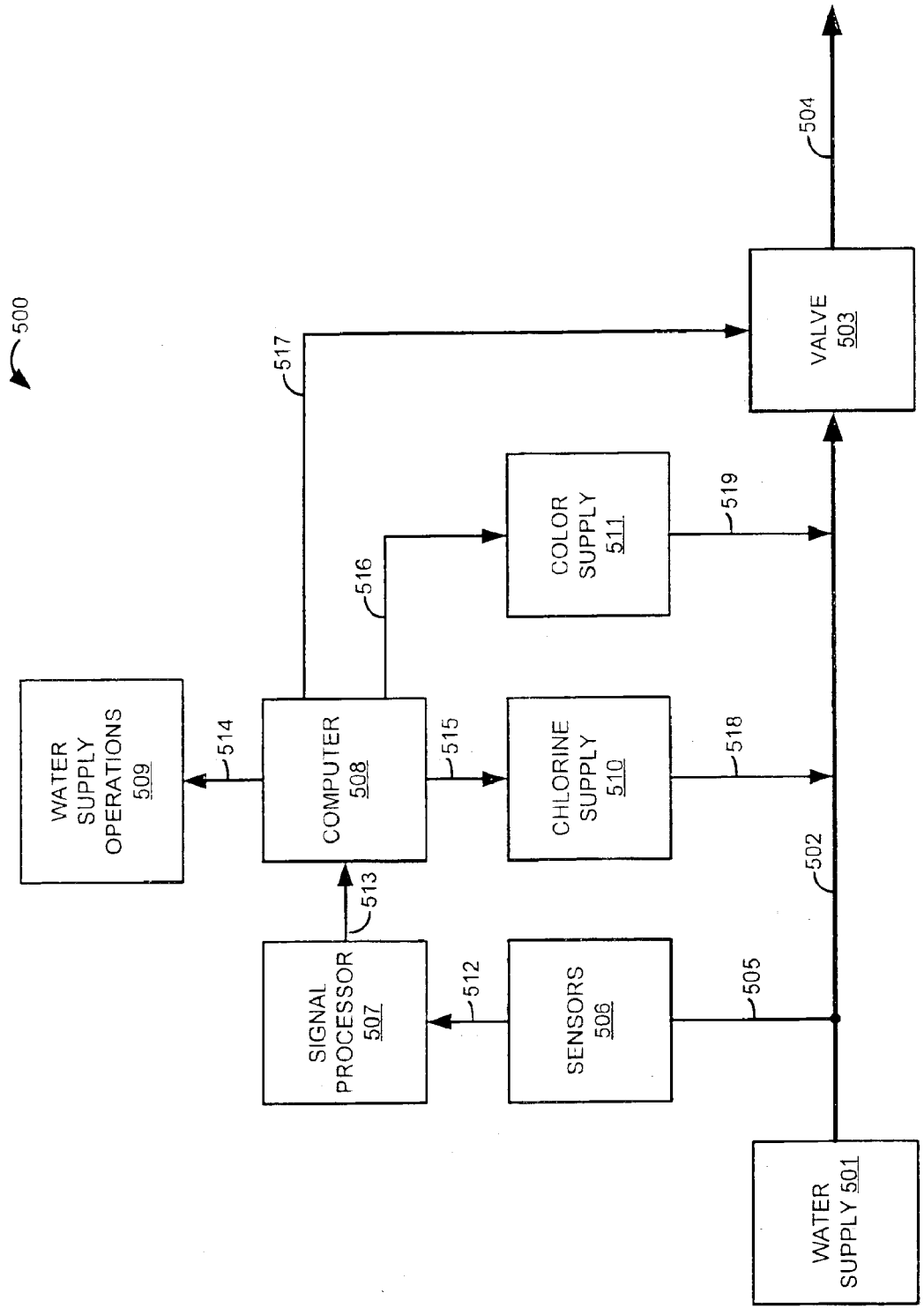
FIG. 5 illustrates a water supply analysis system in an example of the invention.

FIG. 5 illustrates water supply analysis system 500 in an example of the invention. Water supply analysis system 500 includes water supply 501, water main 502, valve 503, water main 504, sample line 505, sensors 506, signal processor 507, computer 508, water supply operations 509, chlorine supply 510, and color supply 511. Water supply 501 provides fresh potable water to water main 502. Under normal operating conditions, valve 503 is open and allows the water to flow from water main 502 to water main 504 for distribution to water users.

Signal processor 507 could be a digital signal processor with firmware. Computer 508 could be a personal computer with software. Signal processor 507 and computer 508 are an example of processing system 105 of FIG. 1. Signal processor 507 is an example of system 201, and computer 508 is an example of systems 202–204 of FIG. 2. Signal processor 507 is an example of elements 301–304 of FIG. 3. Computer 508 is an example of elements 305–309 of FIG. 3 and elements 401–408 of FIG. 4.

Sample line 505 diverts a portion of the water to sensors 506. Sensors 506 measure pH, conductivity, turbidity, chlorine, and total organic carbon in the water from sample line 505. Other measurements could include temperature, pressure, flow rate, dissolved oxygen, oxidation reduction potential, chemical oxygen demand, resistivity, viscosity, ammonia concentration, fluoride, streaming current potential, ultra-violet light absorbance, fluorescence, and sulfide or other ions as measured by ion selective electrodes. Sensors 506 could be separate devices or integrated into a single device. Sensors 506 transfer sensor signals 512 to signal processor 507.

Signal processor 507 processes sensor signals 512 to produce differences 513. Computer 508 processes differences 513 to trigger when a deviation from baseline is detected. In response to the trigger, computer 508 processes the differences to create a process vector and then compares the process vector to a library of vectors to determine if there is a match between the process vector and one of the library vectors. If a match is found, computer 508 classifies the deviation by identifying the operating condition that is associated with the matching library vector.

Based on the classified deviation, computer 508 produces alarms and control signals. Computer 508 transfers alarm 514 indicating the classified deviation to water supply operations 509. In response to unknown classifications, computer 508 may update the vector library as described above.

If the classified deviation is a contaminant in the water, then computer 508 may transfer control signal 515 to chlorine supply 510, and in response, chlorine supply 510 adds chlorine 518 to water main 502 to counter the contaminant. In addition, computer 508 may transfer control signal 516 to color supply 511., and in response, color supply 511 adds colorant 519 to water main 502 to mark the contaminant. For some contaminants, computer 508 may transfer control signal 517 to valve 503, and in response, valve 503 operates to stop the flow of contaminated water to water main 504.

What is claimed is:

1. A method of operating a process analysis system to analyze a process, the method comprising:

in a plurality of sensors, monitoring the process to generate sensor signals that indicate sensor data for the process;

in a processing system, processing the sensor signals to determine a deviation between the sensor data and a baseline for the process;

in the processing system, comparing the deviation to a threshold and generating a trigger if the deviation exceeds the threshold;

in the processing system, generating a process vector representing the deviation; and in the processing system, in response to the trigger, comparing the process vector representing the deviation to a plurality of library vectors representing abnormal operating conditions to classify the deviation.

2. The method of claim 1 wherein the process comprises a system that supplies water.

3. The method of claim 2 wherein the classified deviation comprises a contaminant in the water.

4. The method of claim 2 wherein the sensor signals indicate pH, conductivity, turbidity, chlorine, and total organic carbon of the water.

5. The method of claim 2 further comprising signaling a control system to operate a valve in response to classifying the deviation as a contaminant in the water.

6. The method of claim 2 further comprising signaling a control system to add a marker to the water in response to classifying the deviation as a contaminant in the water.

7. The method of claim 6 wherein the marker comprises a colorant.

8. The method of claim 2 further comprising signaling a control system to perform a treatment on the water in response to classifying the deviation as a contaminant in the water.

9. The method of claim 8 wherein the treatment comprises adding a disinfectant to the water.

10. The method of claim 8 wherein the treatment comprises adding chlorine to the water.

11. The method of claim 8 wherein the treatment comprises exposing the water to ultraviolet radiation.

12. The method of claim 1 wherein processing the sensor signals to detect the deviation and comparing the deviation to the threshold comprises processing the sensor signals to produce a single variable and comparing the single variable to the threshold.

13. The method of claim 1 wherein generating the process vector representing the deviation comprises generating a unit vector.

14. The method of claim 1 wherein comparing the process vector representing the deviation to the library vectors representing the abnormal operating conditions comprises comparing an angle between the process vector and one of the library vectors to another threshold.

15. The method of claim 1 wherein classifying the deviation comprises identifying one of the abnormal operating conditions represented by one of the library vectors that matches the process vector.

16. The method of claim 1 further comprising, in response to an unknown classification, storing the process vector as a new one of the library vectors and associating a new abnormal operating condition with the new library vector.

17. A process analysis system comprising:

a plurality of sensors configured to monitor a process to generate sensor signals that indicate sensor data for the process; and a processing system configured to process the sensor signals to determine a deviation between the sensor data indicated by the sensor signals and a baseline for the process, compare the deviation to a threshold and generate a trigger if the deviation exceeds the threshold, generate a process vector representing the deviation, and in response to the trigger, compare the process vector representing the deviation to a plurality of library vectors representing abnormal operating conditions to classify the deviation.

18. The process analysis system of claim 17 wherein the processing system is configured to process the sensor signals to produce a single variable and compare the single variable to the threshold to detect the deviation and compare the deviation to the threshold.

19. The process analysis system of claim 17 wherein the process vector representing the deviation comprises a unit vector.

20. The process analysis system of claim 17 wherein the processing system is configured to compare an angle between the process vector representing the deviation and one of the library vectors representing one of the abnormal operating conditions to another threshold.

21. The process analysis system of claim 17 wherein the processing system is configured to identify one of the abnormal operating conditions represented by one of the library vectors that matches the process vector to classify the deviation.

22. The process analysis system of claim 17 wherein the processing system is configured to store the process vector representing the deviation as a new one of the library vectors and associate a new abnormal operating condition with the new library vector in response to an unknown classification.

23. The process analysis system of claim 17 wherein the process comprises a system that supplies water.

24. The process analysis system of claim 23 wherein the classified deviation comprises a containment in the water.

25. The process analysis system of claim 24 wherein the processing system is configured to signal a control system to perform a treatment on the water in response to classifying the deviation as a contaminant in the water.

26. The process analysis system of claim 23 wherein the sensor signals indicate pH, conductivity, turbidity, chlorine, and total organic carbon of the water.

27. The process analysis system of claim 23 wherein the processing system is configured to signal a control system to operate a valve in response to classifying the deviation as a contaminant in the water.

28. The process analysis system of claim 23 wherein the processing system is configured to signal the control system to add a marker to the water in response to classifying the deviation as a contaminant in the water.

29. The process analysis system of claim 28 wherein the marker comprises a colorant.

30. The process analysis system of claim 25 wherein the treatment comprises adding a disinfectant to the water.

31. The process analysis system of claim 25 wherein the treatment comprises adding chlorine to the water.

32. The process analysis system of claim 25 wherein the treatment comprises exposing the water to ultraviolet radiation.

* * * * *